US006337199B1

(12) United States Patent
Yum et al.

(10) Patent No.: US 6,337,199 B1
(45) Date of Patent: Jan. 8, 2002

(54) MEMBRANE-BOUND GLUCONATE DEHYDROGENASE, GENE SEQUENCE ENCODING THE SAME AND PRODUCTION OF 2-KETO-D-GLUCONATE USING TRANSFORMED RECOMBINANT E-COLI

(75) Inventors: Do Young Yum; Jae Gu Pan, both of Taejon (KR)

(73) Assignees: Korea Institute of Science and Technology, Seoul; Inbionet Corporation, Taejon, both of (KR)

( * ) Notice: Subject to any disclaimer, the term of this patent is extended or adjusted under 35 U.S.C. 154(b) by 0 days.

(21) Appl. No.: 09/297,937

(22) PCT Filed: Sep. 25, 1998

(86) PCT No.: PCT/KR98/00296

§ 371 Date: May 11, 1999

§ 102(e) Date: May 11, 1999

(87) PCT Pub. No.: WO99/15673

PCT Pub. Date: Apr. 1, 1999

(30) Foreign Application Priority Data

Sep. 25, 1997 (KR) ........................................... 97-48802

(51) Int. Cl.[7] ............................ C12N 9/04; C07K 14/00

(52) U.S. Cl. ....................... 435/190; 435/189; 530/350; 536/23.1; 536/23.2

(58) Field of Search ................................ 435/189, 190; 530/350; 536/23.1, 23.2

(56) References Cited

PUBLICATIONS

Yum et al. Cloning and Expression of a Gene Cluster Encoding Three Subunits of Membrane–Bound Gluconate Dehydrogenase from Erwinia cypripedii ATCC 29267 in *Escherichia coli*, J. Biol. Chem. 179(21): 6566–6572, Nov. 1997.*

T. Sonoyama et al., *Agric. Biol. Chem.*, 51(11), 3039–3047, 1987.

E. Shinagawa et al., *Agric. Biol Chem.*, 48(6), 1517–1522, 1984.

R. Klasen, *Journal of Bacteriology*, 177(10), 2637–2643, May 1995.

S. Anderson et al., *Science*, vol. 230, 144–149, Oct. 11 1985.

J.F. Grindley et al., *App. and Envir. Microbiol.*, 54(7), 1770–1775, Jul. 1988.

S. Truesdell et al., *J. of Bacteriology*, 173(21), 6651–6656, Nov. 1991.

R. Lazarua et al., Vitamin C: Bioconversion via a Recombinant DNA Approach, 187–193.

K. Matsushita et al., [31] D–Gluconate Dehydrogenase from Bacteria, 2–Keto–D–gluconate–Yielding, Membrane–Bound, 187–193.

* cited by examiner

*Primary Examiner*—Rebecca E. Prouty
*Assistant Examiner*—Richard Hutson
(74) *Attorney, Agent, or Firm*—Jacobson Holman, PLLC

(57) ABSTRACT

There is disclosed a novel membrane-bound GADH from *Erwinia cypripedii* ATCC29267, which is useful for the production of 2KDG at high yields under the condition free of intracellular metabolism. 2KDG is converted at high yields from glucose or D-gluconate by culturing a recombinant cell, free of a ketogluconate metabolism, which harbors a recombinant plasmid containing a gene encoding the GADH.

2 Claims, 4 Drawing Sheets

FIG. 2A

AGGCCTTAACTGTCTGTAGGCTGTTGTATCAGACCATGACAATGTCGCGCCTGCGGTGTAAAGCCGCTGCGC 72

AAAATGTTAATTATTTTGTGCGAATTTGTGTCCTTACGCTAAATCTTTGTCATCAACGGTGTTACACTGCGA 144

CGCAATGTTACCGGTAACGGTGGCGCTGTATCCTTAAGCCCGCACATAAAAATCATTACAACGCAATCAGTT 216

AACCTTTCATGCCACATTATATGCGGCACTGAGGCAATGTCATGTCAGAACACAAAAATGGTCACACACGCA 288
M S E H K N G H T R

GGGATTTTCTGCTGAGAACCATCACCCTGGCGCCAGCAATGGCGGTGGGTTCAACAGCGATGGGTGCACTGG 360
R D F L L R T I T L A P A M A V G S T A M G A L

TTGCGCCAATGGCTGCCGGAGCAGCAGAACAAAGCAGCGGGTCACAAACCGCCCGCGACTATCAGCCGACCT 432
V A P M A A G A A E Q S S G S Q T A R D Y Q P T

GGTTTACGGCGGAAGAGTTTGCCTTTATCACCGCAGCGGTGGCACGTCTGATCCCCAACGATGAACGTGGTC 504
W F T A E E F A F I T A A V A R L I P N D E R G

CTGGCGCACTGGAAGCCGGGGTGCCGGAGTTTATCGATCGCCAGATGAACACCCCGTACGCCCTCGGCAGCA 576
P G A L E A G V P E F I D R Q M N T P Y A L G S

ACTGGTACATGCAGGGGCCGTTCAATCCCGATCTGCCGAAAGAGCTGGGTTATCAGCTGCCGCTGGTGCCGC 648
N W Y M Q G P F N P D L P K E L G Y Q L P L V P

AGCAGATCTACCGTCTGGGCCTCGCCGATGCTGATAGCTGGAGCAAACACCAGCACGGCAAAGTGTTTGCTG 720
Q Q I Y R L G L A D A D S W S K H Q H G K V F A

AGCTGAGCGGCGACCAGCAGGATGCCCTGCTGAGCGACTTCGAAAGTGGCAAAGCGGAGTTCACCCAGCTCC 792
E L S G D Q Q D A L L S D F E S G K A E F T Q L

CGGCCAAAACCTTCTTCTCCTTCCTGCTGCAAAACACCCGCGAGGGTTACTTCACGCGATCCGATCCACGGT 864
P A K T F F S F L L Q N T R E G Y F T R S D P R

GGCAATCAGGGCATGGTGGGCTGGAAGCTGATTGGCTTCCCCGGCGCACGCGCTGATTACATGGATTGGGTG 936
W Q S G H G G L E A D W L P R R T R * V

GAACGCGGTGAACGCGTATCCGTTCCCGTCAGTGGATATTCGCGGGGAGAGGGCGTAACCGTGGCAAATGAA 1008
E R G E R V S V P V S G Y S R G E G V T V A N E

TTGAAGAAAGTGGATGCGGTGGTGGTGGGTTTCGGCTGGGCCGGTGCCATCATGGCAAAAGAACTGACCGAA 1080
L K K V D A V V V G F G W A G A I M A K E L T E

GCCGGGCTGAATGTGGTGGCGCTGGAGCGTGGTCCGCATCGTGACACCTACCCGGATGGCGCGTATCCGCAA 1152
A G L N V V A L E R G P H R D T Y P D G A Y P Q

TCCATTGATGAACTGACCTACAACATCCGTAAAAAGCTGTTCCAGGACCTGTCAAAAAGCACCGTCACCATT 1224
S I D E L T Y N I R K K L F Q D L S K S T V T I

CGTCACGACGCGTCACAGACGGCAGTGCCGTATCGTCAGCTGGCGGCGTTTCTGCCCGGCACCGGTACCGGC 1296
R H D A S Q T A V P Y R Q L A A F L P G T G T G

GGCGCGGGCCTGCACTGGTCAGGCGTACATTTCCGTGTCGACCCGGTCGAGCTGAATCTGCGCAGCCATTAT 1368
G A G L H W S G V H F R V D P V E L N L R S H Y

GAAGCGCGTTACGGCAAAAACTTTATCCCGGAAGGCATGACGATTCAGGATTTCGGCGTCAGCTATAACGAA 1440
E A R Y G K N F I P E G M T I Q D F G V S Y N E

CTGGAACCCTTCTTCGATCAGGCGGAGAAAGTCTTTGGTACCTCGGGCAGTGCCTGGACCATCAAAGGCAAG 1512
L E P F F D Q A E K V F G T S G S A W T I K G K

ATGATCGGCAAGGAGAAAGGCGGCAACTTTTACGCGCCGGACCGCTCCAGCGACTTCCCGCTGCCCGCACAG 1584
M I G K E K G G N F Y A P D R S S D F P L P A Q

AAGCGGACTTACTCGGCGCAGCTGTTTGCCCAGGCGGCAGAGTCGGTGGGCTATCATCCGTACGATATGCCA 1656
K R T Y S A Q L F A Q A A E S V G Y H P Y D M P

FIG. 2B

```
TCGGCCAACACCTCAGGTCCGTACACCAACACCTACGGCGCACAGATGGGCCCGTGCAACTTCTGCGGCTAT 1728
 S  A  N  T  S  G  P  Y  T  N  T  Y  G  A  Q  M  G  P  C  N  F  C  G  Y
TGCAGCGGCTACGCCTGCTACATGTATTCCAAAGCGTCGCCTAACGTGAACATCCTGCCCGCGCTGCGTCAG 1800
 C  S  G  Y  A  C  Y  M  Y  S  K  A  S  P  N  V  N  I  L  P  A  L  R  Q
GAGCCGAAGTTTGAGCTGCGTAACAACGCATATGTGTTGCGCGTCAATCTGACCGGCGACAAAAAACGCGCC 1872
 E  P  K  F  E  L  R  N  N  A  Y  V  L  R  V  N  L  T  G  D  K  K  R  A
ACTGGCGTGACCTATCTCGATGGTCAGGGTCGTGAAGTGGTGCAGCCTGCGGATCTGGTGATCCTGTCAGCG 1944
 T  G  V  T  Y  L  D  G  Q  G  R  E  V  V  Q  P  A  D  L  V  I  L  S  A
TTCCAGTTCCACAACGTGCACCTGATGCTGCTGTCCGGTATCGGCCAGCCGTATAACCCGATCACTAACGAA 2016
 F  Q  F  H  N  V  H  L  M  L  L  S  G  I  G  Q  P  Y  N  P  I  T  N  E
GGTGTGGTCGGCCGTAACTTCGCTTATCAGAACATCTCGACGCTGAAAGCGCTGTTCGACAAAAACACCACC 2088
 G  V  V  G  R  N  F  A  Y  Q  N  I  S  T  L  K  A  L  F  D  K  N  T  T
ACTAACCCGTTTATCGGTGCGGGTGGCGCAGGGGTGGCGGTGGATGATTTCAACGCCGACAACTTCGACCAC 2160
 T  N  P  F  I  G  A  G  G  A  G  V  A  V  D  D  F  N  A  D  N  F  D  H
GGCCCGTACGGCTTCGTCGGTGGCTCGCCATTCTGGGTGAACCAGGCGGGTACCAAACCGGTTTCCGGTCTG 2232
 G  P  Y  G  F  V  G  G  S  P  F  W  V  N  Q  A  G  T  K  P  V  S  G  L
CCGACCCCCAAAGGCACGCCGAACTGGGGCAGCCAGTGGAAAGCGGCGGTGGCGGATACCTACAACCACCAT 2304
 P  T  P  K  G  T  P  N  W  G  S  Q  W  K  A  A  V  A  D  T  Y  N  H  H
ATTTCGATGGATGCCCACGGTGCGCACCAGTCATACCGCGCTAACTACCTCGATCTCGATCCGAACTACAAA 2376
 I  S  M  D  A  H  G  A  H  Q  S  Y  R  A  N  Y  L  D  L  D  P  N  Y  K
AATGTCTACGGCCAGCCGCTGCTGCGTATGACCTTTGACTGGCAGGACAACGACATCAGGATGGCGCAGTTT 2448
 N  V  Y  G  Q  P  L  L  R  M  T  F  D  W  Q  D  N  D  I  R  M  A  Q  F
ATGGTCGGCAAGATGCGCAAAATCACCGAGGCCATGAATCCGAAGATGATCATCGGCGGCGCTAAGGGACCG 2520
 M  V  G  K  M  R  K  I  T  E  A  M  N  P  K  M  I  I  G  G  A  K  G  P
GGTACCCACTTCGATACCACCGTGTATCAAACCACGCATATGAGCGGCGGGGCGATCATGGGTGAAGATCCG 2592
 G  T  H  F  D  T  T  V  Y  Q  T  T  H  M  S  G  G  A  I  M  G  E  D  P
AAAACCAGCGCAGTGAACCGTTATTTGCAGAGCTGGGATGTGCCGAACGTGTTTGTGCCGGGTGCGTCCGCG 2664
 K  T  S  A  V  N  R  Y  L  Q  S  W  D  V  P  N  V  F  V  P  G  A  S  A
TTCCCGCAGGGTCTGGGCTACAACCCGACCGGCATGGTGGCGGCACTGACCTACTGGTCGGCGAAAGCCATC 2736
 F  P  Q  G  L  G  Y  N  P  T  G  M  V  A  A  L  T  Y  W  S  A  K  A  I
CGTGAACAGTATCTGAAGAACCCAGGTCCACTGGTGCAGGCATAAGGAAAACGGCGATGATGAAAAGCATTC 2808
 R  E  Q  Y  L  K  N  P  G  P  L  V  Q  A  *                 M  M  K  S  I
TGGCCCTGGTTTTGGGCACGCTGTCGTTCGCCGCGCTGGCGGACGATCAGGCAAATGACGCCCTGGTAAAAC 2880
L  A  L  V  L  G  T  L  S  F  A  A  L  A  D  D  Q  A  N  D  A  L  V  K
GGGGTGAATATCTGGCGCGCGCCGGTGACTGCGTGGCCTGCCACAGCGTCAAAGGTGGGCAGCCTTTTGCCG 2952
R  G  E  Y  L  A  R  A  G  D  C  V  A  C  H  S  V  K  G  G  Q  P  F  A
GTGGGTTGCCGATGGCGACGCCGATTGGCACCATTTATTCCACCAACATCACCCCGGATAAAACCACCGGGA 3024
G  G  L  P  M  A  T  P  I  G  T  I  Y  S  T  N  I  T  P  D  K  T  T  G
TTGGTGACTATAGCTACGACGACTTCCAGAAAGCGGTGCGTCATGGCGTGGCGAAAAACGGTGACACGCTGT 3096
I  G  D  Y  S  Y  D  D  F  Q  K  A  V  R  H  G  V  A  K  N  G  D  T  L
ATCCGGCGATGCCGTATCCGTCTTACGCAGTGGTGAGCGACGAGGACATGAAGGCGCTGTACGCGTACTTTA 3168
Y  P  A  M  P  Y  P  S  Y  A  V  V  S  D  E  D  M  K  A  L  Y  A  Y  F
TGCACGGCGTGGCCCCGGTGGCGCAGGCTAACAAAGACAGCGACATTCCGTGGCCGCTGTCGATGCGCTGGC 3240
M  H  G  V  A  P  V  A  Q  A  N  K  D  S  D  I  P  W  P  L  S  M  R  W
CTTTAGCTATCTGGCGCGGCGTGTTTGCGCCGGACGTGAAAGCGTTCCAGCCTGCCGCCCAGGAAGATCCGG 3312
P  L  A  I  W  R  G  V  F  A  P  D  V  K  A  F  Q  P  A  A  Q  E  D  P
TGCTGGCACGGGGTCGTTATCTGGTGGAAGGTCTGGGTCACTGTGGCGCCTGCCATACGCCGCGCAGCATCA 3384
V  L  A  R  G  R  Y  L  V  E  G  L  G  H  C  G  A  C  H  T  P  R  S  I
```

FIG. 2C

```
CCATGCAGGAGAAAGCGCTCAGCAATGATGGCGCGCATGATTATCTCTCCGGCAGCAGCGCACCGATTGATG 3456
T  M  Q  E  K  A  L  S  N  D  G  A  H  D  Y  L  S  G  S  S  A  P  I  D
GCTGGACCGCAAGCAACCTGCGTGGTGACAACCGCGACGGCCTGGGACGCTGGAGCGAGGACGATCTGCGCC 3528
G  W  T  A  S  N  L  R  G  D  N  R  D  G  L  G  R  W  S  E  D  D  L  R
AGTTCCTGCGCTATGGCCGCAACGATCACACCGCCGCGTTTGGTGGTATGACTGATGTGGTGGAGCACAGCC 3600
Q  F  L  R  Y  G  R  N  D  H  T  A  A  F  G  G  M  T  D  V  V  E  H  S
TGCAACACCTGAGCGATGACGATATCACGGCAATTGCCCGTTATCTGAAGTCGCTGGGGGCGAAGGACGCCA 3672
L  Q  H  L  S  D  D  D  I  T  A  I  A  R  Y  L  K  S  L  G  A  K  D  A
GCCAGACGGTGTTTACCCAGGATGACCAGGTGGCGAAAGCGTTGTGGAAAGGTGATGACAGCCAGACTGGCG 3744
S  Q  T  V  F  T  Q  D  D  Q  V  A  K  A  L  W  K  G  D  D  S  Q  T  G
CGTCGGTGTATGTCGACAGCTGTGCGGCCTGCCATAAAACCGACGGCAGCAGGTTATCAGCGCTTCTTCCCG 3816
A  S  V  Y  V  D  S  C  A  A  C  H  K  T  D  G  S  R  L  S  A  L  L  P
GCGCTGCGTGGCAACCCGGTGGTGCTGGCGAACCCGATCCGACGTCGCTGATCCACATCGTGCTGACTGGCG 3888
G  A  A  W  Q  P  G  G  A  G  E  P  D  P  T  S  L  I  H  I  V  L  T  G
GAACGCTGCCAGGCGTGCAGGGTGCACCGACGGCGATCACCATGCCGGCATTCGGCTGGCGCCTGAATGACC 3960
G  T  L  P  G  V  Q  G  A  P  T  A  I  T  M  P  A  F  G  W  R  L  N  D
AGCAGGTGGCGGATGTTGTGAACTTTATTCGCGGCAGCTGGGGCAACGGTGCCAAAGCCACGGTGACGGCGA 4032
Q  Q  V  A  D  V  V  N  F  I  R  G  S  W  G  N  G  A  K  A  T  V  T  A
AAGATGTCGCATCCTTACGTAAGGATGAAACCGTGCAGGCGCACCAGGGTAATGCGGATATTAAGGTGCTGG 4104
K  D  V  A  S  L  R  K  D  E  T  V  Q  A  H  Q  G  N  A  D  I  K  V  L
AGCAACAGCAGTAATATTACGTTTGCCACGAGGGGATTTCGTTCGCCTCGGAGTGATTTCGTTCGCTATGGG 4176
E  Q  Q  Q  *
CACTGGCAGTTTCAGCTCGCCAGTGCGGCGACCGAGCAAAGGGGACCTGGCCGTCCCCTTTGCATTCCCCGG 4248

CCTTGCGCCGCCTTCCTCGCCGCTTCGCGGCTTTTTCGCGCGATAAATCGCGCCGCTACACGCCGCCTTTCG 4320

CCGCATCCTTGCGGCTCATCCTGGAATCGCTCCCGCGCTCAGCGAGTCCGGATGGCGCTCACACCCCCGCTG 4392

CAACCGCGATGACGGTCTTTGGTTTTTCTTTTGTTGTTTGTTTTTATGAGATGGTCTTGCAGACGGCGGTGT 4464

TGGCGGCATTCGCAGCGCCGAGTGCAGAAGGAAGGCCAGGACGAGTCGCATGGATGCGACGAGAGCGCGGCA 4536

TGGCGCGGATTGCAAAGGTCCGCGCCCTCGGACCTTTGCCCGTCCGCCTGCACAGGCGGCCCTGAAACTGCC 4608

TAAAGCCTGGCGGGCGGAACCCCTGCGGAGCTAAACCGGTGCCAGCGATTAAATATT                4665
```

MEMBRANE-BOUND GLUCONATE DEHYDROGENASE, GENE SEQUENCE ENCODING THE SAME AND PRODUCTION OF 2-KETO-D-GLUCONATE USING TRANSFORMED RECOMBINANT E-COLI

TECHNICAL FIELD

The present invention relates to a novel membrane-bound gluconate dehydrogenase (hereinafter referred to as "GADH") from *Erwinia cypripedii* ATCC29267. More particularly, the present invention relates to a GADH, a DNA encoding the same, a recombinant plasmid containing said DNA, a host cell transformed with said recombinant plasmid, and the production of 2-keto-D-gluconate (hereinafter referred to as "2KDG") from glucose or D-gluconate by culturing the recombinant cell.

BACKGROUND ART

Acetic acid bacteria, such as Erwinia, Glucobacter and Acetobacter, use alcohols and aldehydes as oxidizable substrates, converting it to acetic acid. Many carbohydrates, including glucose, glycerol, and sorbitol, and primary and secondary alcohols can also serve as energy sources, their oxidation characteristically resulting in the transient or permanent accumulation of partly oxidized organic products. This oxidation is mediated by membrane-bound dehydrogenases, such as alcohol dehydrogenase or aldehyde dehydrogenase, linked to the respiratory chain located in cytoplasmic membrane of the bacteria. There are two types of membrane-bound dehydrogenases: a quinoprotein and a flavoprotein having pyroroloquinoline quinon (PQQ) and flavin adenine dinucleotide (FAD), respectively, as cofactors. They are linked to the respiratory chain in the cytoplasmic membrane wherein electrons are transferred finally to oxygen, producing energy. Because the membrane-bound dehydrogenases can convert substrate outside the cells in addition to being of high activity for substrate, they have a significant advantage of being relatively high in substrate conversion rate and yield rate.

Much attention has been paid to the bioconversion processes using microorganisms on account that they have advantages over conventional chemical techniques, including economical and ecological aspects. In addition, the great advance which has been achieved in genetic recombination techniques and metabolic engineerings allows the bioconversion processes to overcome the conventional technical problems and to replace complicated chemical processes. The production of vitamin C is a representative example. In current, the production of 2-keto-L-gulonate, a precursor of vitamin C, via the sorbitol pathway or the glucose pathway, has been established or put to practical use.

In several species of the genera, Erwinia, Gluconobacter and Acetobacter, glucose is converted to gluconate, 2-keto-D-gluconate, and 12,5-diketo-D-gluconate by the mediation of glucose dehydrogenase, gluconate dehydrogenase and 2-keto-D-gluconate dehydrogase, respectively, which are linked to cytochrome C located in the cytoplasmic membrane of the bacteria (Ameyma et al., Agric. Biol. Chem. 51:2943–2950, 1987; Sonoyama et al., Agric. Biol. Chem. 52 : 667–674, 1988). 2,5-Diketo-D-gluconate is further converted to 2-keto-L-gulonate by 2,5-diketo-D-gulonate reductase (25DKG reductase). The above microorganisms, however, are disadvantageous tools in the aspect of the production yield of the vitamin C precursor because glucose undergoes both of the oxidative metabolism and the intracellular metabolism through which the intermediate products of the oxidative metabolism are transferrred inside the cell.

DISCLOSURE OF THE INVENTION

Accordingly, it is an object of the present invention to overcome the above problems and to provide a novel membrane-bound GADH form *Erwinia cypripedii* ATCC29267, which is useful for the production of 2KDG at high yields under the condition free of intracellular metabolism.

It is another object of the present invention to provide a novel DNA encoding the GADH.

It is a further object of the present invention to provide a novel recombinant plasmid containing the DNA and a host cell transformed with said recombinant plasmid.

In accordance with the present invention, 2KDG is converted at high yields from glucose or D-gluconate by culturing a recombinant cell, free of a ketogluconate metabolism, which harbors a plasmid containing a gene encoding the GADH.

BRIEF DESCRIPTION OF THE DRAWINGS

The foregoing and other objects, features and advantages of the present invention will become more apparent from the following detailed description when taken in conjunction with the accompanying drawings in which:

FIGS. 2A–2C show nucleotide (SEQ ID NO:12) and deduced amino acid sequences (SEQ ID NO:13) of the genes encoding a dehydrogenase, a cytochrome c, and a third subunit.

BEST MODES FOR CARRYING OUT THE INVENTION

Figure 1:
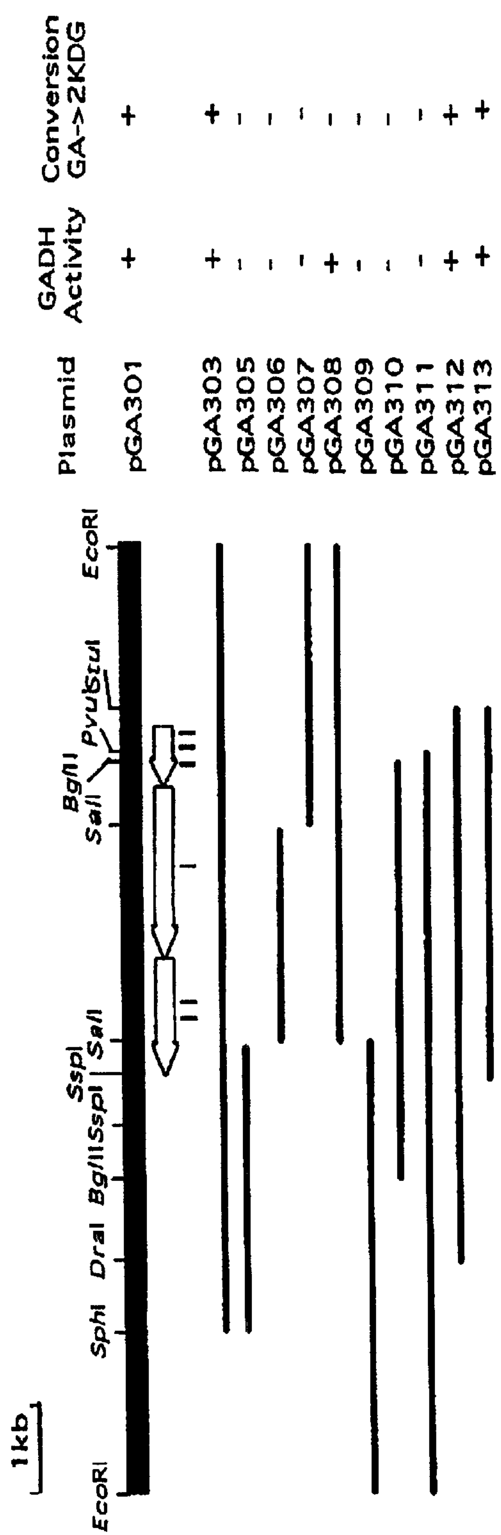
FIG. 1 shows a restriction map of cloned DNA fragment encoding gluconate dehydrogenase gene of *E. cypripedii*.

First Stage: Purification of GADH from *E. cypripedii* ATCC29267 and Amino Terminal Amino Acid sequencing of Subunits

*E. cypripedii* was grown at 30° C. in a medium, which contained $(NH_4)_2SO_4$10 g/l, yeast extract 3 g/l, $KH_2PO_4$ 0.2g/l, $NaH_2PO_4$ 0.8 g/l, trisodium citrate 0.5 g/l, trace metal 1 ml/l, glucose 50 g/l, and $MgSO_4.7H_2O$ 0.7 g/l at pH 6.0–6.5. Cells of *E. cypripedii* were harvested at the late exponential phase and washed twice with water, followed by treatment with homogenizer in 50 mM acetate buffer (pH 5.0). After centrifugation to remove the cell debris, the resulting supernatant was further centrifuged at 80,000×g for 60 min. The precipitate was collected and designated the membrane fraction. The crude membrane fraction was solubilized with 50 mM acetate buffer (pH 5.0) containing 2% Tween 80 and 0.1 M KCl by stirring for 8 hr at 4° C. The supernatant obtained by ultracentrifugation was dialyzed overnight against two changes of 2 liters of 20 mM acetate buffer (pH4.5) containing 0.2% Tween 80. The dialysate was applied to CM-Sepharose CL-6B (Pharmacia) column (3×12 cm) equilibrated with 20 mM acetate buffer containing 0.2% Tween 80 and eluted isocratically with 20 mM acetate buffer (pH4.5) containing 0.2% Tween 80 and 0.1 M NaCl. Active fractions were pooled and dialyzed against 10 mM phosphate buffer (pH 6.0) containing 0.2% Tween 80. The dialysate was applied to DEAE-Toyopearl 650 (Tosoh) column (3×10 cm) equilibrated with a 20 mM acetate buffer (pH 6.0) containing 0.2% Tween 80 and the enzyme gluconate dehydrogenase was eluted with a linear NaCl gradient (0–300 mM) made with a buffer containing 0.2% Tween 80.

SDS-PAGE of the enzyme showed three polypeptides, 65, 45, and 20 kDa, which were designated subunit I, II and III, respectively. The $NH_2$-terminal amino acid sequences of the three subunits were determined as follows:

Subunit I:

NH2-Ala-Asn-Glu-Leu-Lys-Lys-Val-Asp-Ala-Val-Val-Val-Gly-Phe-Gly (SEQ ID NO:1)

Subunit II: NH2-Asp-Asp-Gln-Ala-Asn-Asp-Ala-Leu-Val (SEQ ID NO:2)

Subunit III: NH2-Ala-Glu-Gln-Ser-Ser-Gly-Ser-Gln-Thr-Ala-Arg-Asp-Tyr-Gln-Pro (SEQ ID NO:3)

Second Stage: Cloning of the Gene Encoding GADH

The genome DNA of *E. cypripedii* was partially digested with EcoRI and only the DNA fragments larger than 10 kb were ligated to the pUC19 which had been opened by the same restriction enzyme. After being introduced with the ligates, *E. coli* JM109 was spread on LB media containing ampicillin 100 μg/ml. The colonies grown were transferred to nitrocellulose filters which were, then, placed on a 3 MM paper soaked in the GADH activity assay mixture (50 mM acetate buffer, pH5.0, 1 mM phenazine methosulfate (PMS), 1.5 mM 2,6-dichlorophenol indophenol (DCPIP), 0.5% Triton X-100, 0.2 M D-gluconate.Na). The GADH positive clones were identified by the yellow zones that formed around the colony on the filter under a purple background, which indicated the areas where membrane-bound dehydrogenase catalyzed D-gluconate-dependent reduction of dichlorophenolindophenol (DCPIP). Out of 4,000 transformants, one putative positive clone was isolated by a direct expression method and designated 301. This recombinant clone was further checked whether it produces 2KDG in the medium of LB containing D-gluconate by subjecting its products to HPLC. A plasmid was purified from the positive recombinant strain by an alkali method (Sambrook, J., et al., Molecular Cloning, CSH Press, p. 1.25, 1989) and found to contain a 10.5 kb DNA insert as digested with EcoRI. The plasmid containing the DNA insert was designated pGA301. By use of various restriction enzymes, a restriction map for the cloned 10.5 kb EcoRI fragment was made as shown in FIG. 1. In FIG. 1, the open arrows indicate the coding sequence for a dehydrogenase (subunit I), a cytochrome c (II), and the smallest subunit (III). Plasmids of pGA series are presented under the restriction map. Enzyme activity was assayed using ferricyanide as an electron acceptor. Conversion activity was assayed by HPLC.

Third Stage Sub-Cloning of the DNA Fragments Encoding GDH A series of deletion clones of pGA301 (pGA303, 304, 305, 306, 307, 308, 309, 310, 311, 312 and 313) were constructed by subcloning the restriction fragments into pUC and pBluescript vectors in order to find out the smallest DNA fragment which is able to convert GDH to 2KDH. As shown in FIG. 1, the StuI-SspI DNA fragment 4.7 kb long was found to be the smallest fragment necessary for the conversion in the light of the fact that *E. coli* cells harboring pGA303, pGA308, pGA312, and pGA313 showed the dehydrogenase activity by the ferricyanide method while *E. coli* cells harboring pGA308 among them did not convert D-gluconate to 2KDG. These results indicated that the 4.7 kb StuI-SspI DNA fragment covered the whole dehydrogenase subunit gene.

The *E. Coli* JM109 harboring the recombinant plasmid pGA313 was deposited in Genetic Resources Center, Korean Research Institute of Bioscience and Biotechnology of the Korean Institute of Science and Technology on Aug. 8, 1998 and received a Deposition No. KCTC 0521BP.

Fourth Stage: DNA Sequence Analysis of a Gene cluster Encoding the Three Subunits of GADH Nucleotide sequence analysis was performed with the aid of the DNASIS program by the dideoxy chain termination method (Sanger et al, Proc. Natl. Acad. Sci. USA., 74:5463–5467 (1977)). Both strands were sequenced with synthetic oligonucleotide primers as needed. The DNA sequence was analyzed with the aid of the DNASIS sequence analysis program (Hitachi Software Engineering, CA). The DNA sequence of the 4.7 kb fragment was determined by Edman degradation procedure, and the results are shown in FIG. 2. The vertical arrows indicate the putative signal sequence cleavage sites. Potential ribosome-binding sequences (SD) are marked. Facing arrows show an inverted repeat, which possibly serves as a rho-independent transcriptional terminator. The putative FAD-binding motif is indicated by a dotted underline. The possible heme-binding motifs (C-X-X-C-H) (SEQ ID NO:4) are boxed. The nucleotide sequencing revealed the presence of three open reading frames (ORFs) corresponding to the dehydrogenase subunit (subunit I), the cytochrome c subunit (subunit II), and the smallest subunit (subunit III). The dehydrogenase subunit is located immediately downstream of the gene coding for the smallest subunit, and the cytochrome c subunit in the next. The three subunit genes were organized in the same transcriptional polarity. The two inverted-repeat sequences of possible transcriptional terminators were found downstream of the cytochrome c subunit gene, which may serve as the rho-independent transcriptional terminator. This indicates that these three genes are in the same operon and are co-transcribed.

The ORF corresponding to the subunit III might start with either ATG (nt 258–260), ATG (nt 327–329), ATG (nt 348–350) or ATG (nt 369–371) and terminate at TGA (nt 918–920). The ATG (nt 258–260) seems to be the functional initiator because this ATG was preceded by a possible ribosome-binding sequence, GAGG (nt 247–250). The gene consists of 663 bp, encoding a polypeptide of 221 amino acids, with a calculated molecular weight of 24,471. The NH2-terminal amino acid sequence of the purified smallest subunit was found in this ORF at position 43 to 56. The extra 42 amino acids at NH2-terminus of this ORF showed features typical of leader peptides. The molecular mass of the processed subunit deduced from the nucleotide sequence (20 kDa) coincided well with that estimated by SDS-polyacrylamide gel electrophoresis (20 kDa). The coding region of the predicted dehydrogenase gene probably starts with an GTG codon at positions 934 to 936, preceded by an SD sequence ATGGA. Another possibility is the ATG codon positioned at 925 to 927, but it lacks an SD sequence. The dehydrogenase gene consists of 1,845 bp, encoding a polypeptide of 615 amino acids, with a calculated molecular weight of 67,238. The NH2-terminal amino acid sequence of the purified dehydrogenase subunit was found in this ORF at position 23 to 37. The extra 22 amino acids at NH2-terminus of this ORF also showed features typical of leader peptides. The molecular mass of the mature subunit (64.9 kDa) was in good agreement with that obtained by SDS-polyacrylamide gel electrophoresis (65 kDa).

The ORF corresponding to the cytochrome c subunit II was found 11 bp downstream of the ORF coding for the 67 kDa dehydrogenase subunit. A possible ribosome-binding sequence, AGGA, was present 8 nt upstream of the ATG codon. This ORF encodes a 441 amino acid polypeptide with a molecular weight of 47,094 Da. The NH2-terminal amino acid sequence of the cytochrome c subunit was found in this ORF at position 20 to 28. The extra 19 amino acids at NH2-terminus of this ORF also showed features typical of leader peptides. The molecular mass of the mature subunit (45 kDa) also coincided well with that estimated by SDS-polyacrylamide gel electrophoresis (45 kDa).

The FAD-dependent enzymes possess the characteristic β1-αA-β2 motif for binding the ADP moiety of FAD (Wierenga et al, J. Mol. Biol., 187:101–107 (1986)). This motif is usually located at the amino-terminus of the enzyme, and contains a so-called glycine box (GXGXXG). The deduced amino acid sequence of GADH dehydrogenase subunit I contained three possible glycine boxes at GFGWAG (nt 1036–1053), GTGTGG (nt 1282–1299), and GAGGAG (nt 2104–2121). A homology search against protein databases revealed that the region containing the first glycine box showed a sequence similarity with the FAD-binding motif of cellobiose dehydrogenase (CEDH) from *Phanerochaete chrysosporium* (Li et al, Appl. Environ. Microbiol., 62:1329–1335 (1996), Raices et al, FEBS Lett., 369:233–8 (1995)), sorbose dehydrogenase (SDH) from *Gluconobacter oxydans* (Saito et al, Appl. Environ. Microbiol., 63:454–460 (1987)), choline dehydrogenase (CDH) of *Rhizobium meliloti,* glucose dehydrogenase of *Drosophila melanogaster* (Whetten et al, Genetics, 120:475–484 (1988)), human monoamine oxidase B (Grimsby et al, Proc. Natl. Acad. Sci. U S A., 88:3637–3641 (1991)), and versicolorin B synthase (VBS) from *Aspergillus parasiticus* (Silva et al, J. Biol. Chem., 271:13600–13608 (1996)). This data could indicate that the GADH from *E. cypripedii* is also a flavoprotein like other membrane-bound GADHs (Matsushita et al, J. Biochem., (Tokyo) 85:1173–1181 (1979), Matsushita et al, Methods in Enzymol., 89:187–193 (1982), McIntire et al, Biochem. J., 231:651–654 (1985), Shinagawa et al, Agric. Biol. Chem., 48:1517–1522 (1984)). This homology is a strong evidence that GADH dehydrogenase subunit I has an FAD as a cofactor. By reference, the FAD-binding motif at amino terminus has the following characteristic sequence: Asp-X-X-X-X-Gly-X-Gly-X-X-Gly-X-X-X-Ala-X-X-Leu-X-Glu-X-X-X-X-X-Val-X-X-Glu-X-Gly (SEQ ID NO:5).

In the deduced amino acid sequence of the dehydrogenase subunit, another conserved region with CEDH, SDH, CDH, and VBS was found. However, this region did not reveal any functional domain in the Prosite search. The predicted amino acid sequence of the cytochrome c subunit II showed considerable identity with those of the *G. suboxydans* cytochrome c-553 (34.1%) (Takeda and Shimizu, J. Ferment. Bioeng., 72:1–6 (1991)), *Acetobacter pasteurianus* alcohol dehydrogenase (ADH) cytochrome c (37.2%) (Takemura et al, J. Bacteriol., 175:6857–6866 (1993)), *A. polyoxogenes* ADH cytochrome c (39.3%) (Tamaki et al, Biochim. Biophys. Acta, 1088:292–300 (1991)), and *A. aceti* ADH cytochrome c (38.9%) (Inoue et al, J. Ferment. Bioeng., 73:419–424 (1992)), which also have signal peptides.

Besides, three possible heme-binding motifs (C-X-X-C-H) (SEQ ID NO:5) (Meyer and Kamen, Protein Chem., 35:105–212 (1982)) (nt 2910–2924, 3354–3368 and 3765–3779), which show the characteristic amino acid sequence of the c-type cytochrome, were present within this ORF (FIG. 2). The three regions with a C-X-X-C-H (SEQ ID NO:4) sequence are highly conserved.

As apparent from the above data, *Erwinia cypripedii* ATCC29267 harbors a gene cluster encoding the three subunits of GADH, subunits I, II and III 1,845 bp, 1,323 bp and 663 bp long, respectively, within the 4.7 kb StuI-SspI DNA fragment. The base sequences were registered as U97665 in GeneBank on Apr. 16, 1997.

Fifth Stage: Conversion of Glucose or Gluconate to 2KDG in *E. coli*

*E. coli* K-12 derivatives are capable of synthesizing the apo-glucose dehydrogenase (apo-GDH) but not the cofactor pyrroloquinoline quinone (PQQ), which is essential for the formation of the holo enzyme (Biville et al, J. Gen. Microbiol., 137:1775–1782 (1991), Goosen et al, J. Bacteriol., 171:447–455 (1989)). When PQQ is present in the medium, the holo enzyme is known to be reconstituted, then *E. coli* is capable of oxidizing glucose to gluconate (Hommes et al, FEMS Microbiol. Lett., 24:2–3 (1984)). It has also been reported that the expression of PQQ synthase genes in *E. coli* resulted in GDH activity in the absence of exogenous PQQ (Liu et al, J. Bacteriol., 174:5814–5819 (1992)). Therefore, we tried to convert D-glucose to 2KDG via D-gluconate by a recombinant *E. coli* harboring the cloned GADH gene in the presence of PQQ. The *E. coli* JM109 transformed with pGA313 was cultivated in an LB medium containing 2.5% glucose, 10 μM PQQ, and ampicillin (100 μg/ml). The supernatant was used for assaying the amounts of D-gluconate.Na, and 2KDG.Na converted from D-glucose. The results are shown in Table 1. With *E. coli* JM109 transformed with pUC18 as a control, the glucose was completely converted to 29.9 mg/ml of D-gluconate in 12 hr cultivation by an the addition of PQQ in the culture medium. With *E. coli* JM109 (pGA313) in the presence of PQQ, the glucose (25 mg/ml) was almost completely converted to 29.2 mg/ml of 2-KDG.Na via D-gluconate during 12 hr cultivation. When the culture was carried out with D-gluconate.Na as a carbon source, 30 mg/ml of D-gluconate.Na was converted to 29.2 mg/ml of 2KDG.Na in 12 hr. The conversion yields for D-glucose and D-gluconate were 0.86 mole 2KDG/mole D-glucose and 0.95 mole 2KDG/mole D-gluconate, respectively. D-Glucose (25 mg/ml) was converted to 2KDG with a yield of 0.95 mole 2KDG/mole glucose in 16 hr after inoculation.

TABLE 2

Production of 2KDG in recombinant strains of *E. coli**[1]

| Strains | Sub. | PQQ | Amount (mg/ml in broth) Glu | GA · Na | 2KDG · Na | $Y_{GA}$*[2] | $Y_{GB}$*[2] |
|---|---|---|---|---|---|---|---|
| *E. coli* JM109 (pUC18) | Glu | – | 23.5 | 0 | 0 | 0 | 0 |
| | Glu | + | 0 | 29.9 | 0 | 0.99 | 0 |
| *E. coli* JM109 (pGA313) | Glu | – | 23.5 | 0 | 0 | 0 | 0 |
| | Glu | + | 0 | 2.4 | 25.9 | 0.88 | 0.86 (0.95*[3]) |
| *E. coli* JM109 (pUC18) | GA | – | | 29.8 | 0 | | |

TABLE 2-continued

Production of 2KDG in recombinant strains of *E. coli**1

| Strains | Sub. | PQQ | Amount (mg/ml in broth) | | | | |
|---|---|---|---|---|---|---|---|
| | | | Glu | GA · Na | 2KDG · Na | $Y_{GA}$*2 | $Y_{GB}$*2 |
| *E. coli* JM109 (pGA313) | GA | – | | 0 | 29.2 | | |

*1 *E. coli* strains were cultivated in LB medium containing 2.5% D-glucose (Glu) or D-gluconate (GA) for 12 hr at 37° C.. If needed, PQQ was added to a final concentration of 10 mM.
*2 Molar yields of GA and 2KDG calculated from initial substrate concentration.
*3 Cultivation for 16 hr

INDUSTRIAL APPLICABILITY

Taken together, the data suggested above show that the GDH gene inserted in the plasmid pGA313 is well expressed and glucose is converted to 2KDG at high rates with high yields in the transformed *E. coli.* In addition, the conversion of D-glucose to 2KDG via D-gluconate by a recombinant *E. coli* harboring apo-GDH gene, but not the cofactor PQQ gene, is possible when the *E. coli* is cultivated in a medium supplemented with PQQ because enzyme reconstitution occurs. Therefore, considering the fact that the conversion of D-glucose to 2KDG in *E. coli* not having a ketogluconate metabolism was extremely efficient, the bioconversion process using *E. coli* cells according to the present invention should be useful in genetic engineerings and the food industry.

What is claimed is:

1. An isolated and purified membrane-bound gluconate dehydrogenase from *Erwinia cypripedii* ATCC 29267 having the amino acid sequence of SEQ. ID NO.: 13.

2. The isolated and purified membrane-bound gluconate dehydrogenase as set forth in claim 1, wherein the enzyme has a flavin adenine dinucleotide as a cofactor.

* * * * *

SEQUENCE LISTING

```
<160> NUMBER OF SEQ ID NOS: 13

<210> SEQ ID NO 1
<211> LENGTH: 15
<212> TYPE: PRT
<213> ORGANISM: Erwinia cypripedii

<400> SEQUENCE: 1

Ala Asn Glu Leu Lys Lys Val Asp Ala Val Val Val Gly Phe Gly
  1               5                  10                  15


<210> SEQ ID NO 2
<211> LENGTH: 9
<212> TYPE: PRT
<213> ORGANISM: Erwinia cypripedii

<400> SEQUENCE: 2

Asp Asp Gln Ala Asn Asp Ala Leu Val
  1               5


<210> SEQ ID NO 3
<211> LENGTH: 15
<212> TYPE: PRT
<213> ORGANISM: Erwinia cypripedii

<400> SEQUENCE: 3

Ala Glu Gln Ser Ser Gly Ser Gln Thr Ala Arg Asp Tyr Gln Pro
  1               5                  10                  15


<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: binding
      motif
<223> OTHER INFORMATION: Xaa at various positions throughout the
      sequence may be any amino acid.
```

-continued

```
<400> SEQUENCE: 4

Cys Xaa Xaa Cys His
  1               5


<210> SEQ ID NO 5
<211> LENGTH: 31
<212> TYPE: PRT
<213> ORGANISM: Artificial Sequence
<220> FEATURE:
<223> OTHER INFORMATION: Description of Artificial Sequence: binding
      motif
<223> OTHER INFORMATION: Xaa at various positions throughout the
      sequence may be any amino acid.

<400> SEQUENCE: 5

Asp Xaa Xaa Xaa Xaa Gly Xaa Gly Xaa Xaa Gly Xaa Xaa Xaa Ala Xaa
  1               5                  10                  15

Xaa Leu Xaa Glu Xaa Xaa Xaa Xaa Xaa Val Xaa Xaa Glu Xaa Gly
             20                  25                  30


<210> SEQ ID NO 6
<211> LENGTH: 660
<212> TYPE: DNA
<213> ORGANISM: Erwinia cypripedii

<400> SEQUENCE: 6

atgtcagaac acaaaaatgg tcacacacgc agggattttc tgctgagaac catcaccctg     60

gcgccagcaa tggcggtggg ttcaacagcg atgggtgcac tggttgcgcc aatggctgcc    120

ggagcagcag aacaaagcag caaatcacaa accgcccgcg actatcagcc gacctggttt    180

acggcggaag agtttgcctt tatcaccgca gcggtggcac gtctgatccc caacgatgaa    240

cgtggtcctg gcgcactgga agccggggtg ccggagttta tcgatcgcca gatgaacacc    300

ccgtacgccc tcggcagcaa ctggtacatg caggggccgt tcaatcccga tctgccgaaa    360

gagctgggtt atcagctgcc gctggtgccg cagcagatct accgtctggg cctcgccgat    420

gctgatagct ggagcaaaca ccagcacggc aaagtgtttg ctgagctgag cggcgaccag    480

caggatgccc tgctgagcga cttcgaaagt ggcaaagcgg agttcaccca gctcccggcc    540

aaaaccttct tctccttcct gctgcaaaac acccgcgagg gttacttcac gcgatccgat    600

ccacggtggc aatcagggca tggtgggctg gaagctgatt ggcttccccg gcgcacgcgc    660


<210> SEQ ID NO 7
<211> LENGTH: 220
<212> TYPE: PRT
<213> ORGANISM: Erwinia cypripedii

<400> SEQUENCE: 7

Met Ser Glu His Lys Asn Gly His Thr Arg Arg Asp Phe Leu Leu Arg
  1               5                  10                  15

Thr Ile Thr Leu Ala Pro Ala Met Ala Val Gly Ser Thr Ala Met Gly
             20                  25                  30

Ala Leu Val Ala Pro Met Ala Ala Gly Ala Ala Glu Gln Ser Ser Lys
         35                  40                  45

Ser Gln Thr Ala Arg Asp Tyr Gln Pro Thr Trp Phe Thr Ala Glu Glu
     50                  55                  60

Phe Ala Phe Ile Thr Ala Ala Val Ala Arg Leu Ile Pro Asn Asp Glu
 65                  70                  75                  80

Arg Gly Pro Gly Ala Leu Glu Ala Gly Val Pro Glu Phe Ile Asp Arg
                 85                  90                  95
```

-continued

```
Gln Met Asn Thr Pro Tyr Ala Leu Gly Ser Asn Trp Tyr Met Gln Gly
            100                 105                 110

Pro Phe Asn Pro Asp Leu Pro Lys Glu Leu Gly Tyr Gln Leu Pro Leu
        115                 120                 125

Val Pro Gln Gln Ile Tyr Arg Leu Gly Leu Ala Asp Ala Asp Ser Trp
    130                 135                 140

Ser Lys His Gln His Gly Lys Val Phe Ala Glu Leu Ser Gly Asp Gln
145                 150                 155                 160

Gln Asp Ala Leu Leu Ser Asp Phe Glu Ser Gly Lys Ala Glu Phe Thr
                165                 170                 175

Gln Leu Pro Ala Lys Thr Phe Phe Ser Phe Leu Leu Gln Asn Thr Arg
            180                 185                 190

Glu Gly Tyr Phe Thr Arg Ser Asp Pro Arg Trp Gln Ser Gly His Gly
        195                 200                 205

Gly Leu Glu Ala Asp Trp Leu Pro Arg Arg Thr Arg
    210                 215                 220
```

<210> SEQ ID NO 8
<211> LENGTH: 1845
<212> TYPE: DNA
<213> ORGANISM: Erwinia cypripedii

<400> SEQUENCE: 8

```
gtggaacgcg gtgaacgcgt atccgttccc gtcagtggat attcgcgggg agagggcgta      60

accgtggcaa atgaattgaa gaaagtggat gcggtggtgg tgggtttcgg ctgggccggt     120

gccatcatgg caaaagaact gaccgaagcc gggctgaatg tggtggcgct ggagcgtggt     180

ccgcatcgtg acacctaccc ggatggcgcg tatccgcaat ccattgatga actgacctac     240

aacatccgta aaaagctgtt ccaggacctg tcaaaaagca ccgtcaccat tcgtcacgac     300

gcgtcacaga cggcagtgcc gtatcgtcag ctggcggcgt ttctgcccgg caccggtacc     360

ggcggcgcgg gcctgcactg gtcaggcgta catttccgtg tcgacccggt cgagctgaat     420

ctgcgcagcc attatgaagc gcgttacggc aaaaacttta tcccggaagg catgacgatt     480

caggatttcg gcgtcagcta taacgaactg gaacccttct tcgatcaggc ggagaaagtc     540

tttggtacct cgggcagtgc ctggaccatc aaaggcaaga tgatcggcaa ggagaaaggc     600

ggcaactttt acgcgccgga ccgctccagc gacttcccgc tgcccgcaca gaagcggact     660

tactcggcgc agctgtttgc ccaggcggca gagtcggtgg gctatcatcc gtacgatatg     720

ccatcggcca acacctcagg tccgtacacc aacacctacg gcgcacagat gggcccgtgc     780

aacttctgcg gctattgcag cggctacgcc tgctacatgt attccaaagc gtcgcctaac     840

gtgaacatcc tgcccgcgct gcgtcaggag ccgaagtttg agctgcgtaa caacgcatat     900

gtgttgcgcg tcaatctgac cggcgacaaa aaacgcgcca ctggcgtgac ctatctcgat     960

ggtcagggtc gtgaagtggt gcagcctgcg gatctggtga tcctgtcagc gttccagttc    1020

cacaacgtgc acctgatgct gctgtccggt atcggccagc cgtataaccc gatcactaac    1080

gaaggtgtgg tcggccgtaa cttcgcttat cagaacatct cgacgctgaa agcgctgttc    1140

gacaaaaaca ccaccactaa cccgtttatc ggtgcgggtg gcgcaggggt ggcggtggat    1200

gatttcaacg ccgacaactt cgaccacggc ccgtacggct tcgtcggtgg ctcgccattc    1260

tgggtgaacc aggcgggtac caaaccggtt tccggtctgc cgacccccaa aggcacgccg    1320

aactggggca gccagtggaa agcggcggtg gcggatacct acaaccacca tatttcgatg    1380
```

-continued

```
gatgcccacg gtgcgcacca gtcataccgc gctaactacc tcgatctcga tccgaactac   1440

aaaaatgtct acggccagcc gctgctgcgt atgacctttg actggcagga caacgacatc   1500

aggatggcgc agtttatggt cggcaagatg cgcaaaatca ccgaggccat gaatccgaag   1560

atgatcatcg gcggcgctaa gggaccgggt acccacttcg ataccaccgt gtatcaaacc   1620

acgcatatga gcggcggggc gatcatgggt gaagatccga aaaccagcgc agtgaaccgt   1680

tatttgcaga gctgggatgt gccgaacgtg tttgtgccgg gtgcgtccgc gttcccgcag   1740

ggtctgggct acaacccgac cggcatggtg gcggcactga cctactggtc ggcgaaagcc   1800

atccgtgaac agtatctgaa gaacccaggt ccactggtgc aggca                    1845
```

```
<210> SEQ ID NO 9
<211> LENGTH: 615
<212> TYPE: PRT
<213> ORGANISM: Erwinia cypripedii

<400> SEQUENCE: 9

Val Glu Arg Gly Glu Arg Val Ser Val Pro Val Ser Gly Tyr Ser Arg
  1               5                  10                  15

Gly Glu Gly Val Thr Val Ala Asn Glu Leu Lys Lys Val Asp Ala Val
             20                  25                  30

Val Val Gly Phe Gly Trp Ala Gly Ala Ile Met Ala Lys Glu Leu Thr
         35                  40                  45

Glu Ala Gly Leu Asn Val Val Ala Leu Glu Arg Gly Pro His Arg Asp
     50                  55                  60

Thr Tyr Pro Asp Gly Ala Tyr Pro Gln Ser Ile Asp Glu Leu Thr Tyr
 65                  70                  75                  80

Asn Ile Arg Lys Lys Leu Phe Gln Asp Leu Ser Lys Ser Thr Val Thr
                 85                  90                  95

Ile Arg His Asp Ala Ser Gln Thr Ala Val Pro Tyr Arg Gln Leu Ala
            100                 105                 110

Ala Phe Leu Pro Gly Thr Gly Thr Gly Gly Ala Gly Leu His Trp Ser
        115                 120                 125

Gly Val His Phe Arg Val Asp Pro Val Glu Leu Asn Leu Arg Ser His
    130                 135                 140

Tyr Glu Ala Arg Tyr Gly Lys Asn Phe Ile Pro Glu Gly Met Thr Ile
145                 150                 155                 160

Gln Asp Phe Gly Val Ser Tyr Asn Glu Leu Glu Pro Phe Phe Asp Gln
                165                 170                 175

Ala Glu Lys Val Phe Gly Thr Ser Gly Ser Ala Trp Thr Ile Lys Gly
            180                 185                 190

Lys Met Ile Gly Lys Glu Lys Gly Gly Asn Phe Tyr Ala Pro Asp Arg
        195                 200                 205

Ser Ser Asp Phe Pro Leu Pro Ala Gln Lys Arg Thr Tyr Ser Ala Gln
    210                 215                 220

Leu Phe Ala Gln Ala Ala Glu Ser Val Gly Tyr His Pro Tyr Asp Met
225                 230                 235                 240

Pro Ser Ala Asn Thr Ser Gly Pro Tyr Thr Asn Thr Tyr Gly Ala Gln
                245                 250                 255

Met Gly Pro Cys Asn Phe Cys Gly Tyr Cys Ser Gly Tyr Ala Cys Tyr
            260                 265                 270

Met Tyr Ser Lys Ala Ser Pro Asn Val Asn Ile Leu Pro Ala Leu Arg
        275                 280                 285

Gln Glu Pro Lys Phe Glu Leu Arg Asn Asn Ala Tyr Val Leu Arg Val
```

-continued

```
    290                 295                 300

Asn Leu Thr Gly Asp Lys Lys Arg Ala Thr Gly Val Thr Tyr Leu Asp
305                 310                 315                 320

Gly Gln Gly Arg Glu Val Val Gln Pro Ala Asp Leu Val Ile Leu Ser
                325                 330                 335

Ala Phe Gln Phe His Asn Val His Leu Met Leu Leu Ser Gly Ile Gly
            340                 345                 350

Gln Pro Tyr Asn Pro Ile Thr Asn Glu Gly Val Val Gly Arg Asn Phe
        355                 360                 365

Ala Tyr Gln Asn Ile Ser Thr Leu Lys Ala Leu Phe Asp Lys Asn Thr
    370                 375                 380

Thr Thr Asn Pro Phe Ile Gly Ala Gly Gly Ala Gly Val Ala Val Asp
385                 390                 395                 400

Asp Phe Asn Ala Asp Asn Phe Asp His Gly Pro Tyr Gly Phe Val Gly
                405                 410                 415

Gly Ser Pro Phe Trp Val Asn Gln Ala Gly Thr Lys Pro Val Ser Gly
            420                 425                 430

Leu Pro Thr Pro Lys Gly Thr Pro Asn Trp Gly Ser Gln Trp Lys Ala
        435                 440                 445

Ala Val Ala Asp Thr Tyr Asn His His Ile Ser Met Asp Ala His Gly
    450                 455                 460

Ala His Gln Ser Tyr Arg Ala Asn Tyr Leu Asp Leu Asp Pro Asn Tyr
465                 470                 475                 480

Lys Asn Val Tyr Gly Gln Pro Leu Leu Arg Met Thr Phe Asp Trp Gln
                485                 490                 495

Asp Asn Asp Ile Arg Met Ala Gln Phe Met Val Gly Lys Met Arg Lys
            500                 505                 510

Ile Thr Glu Ala Met Asn Pro Lys Met Ile Ile Gly Gly Ala Lys Gly
        515                 520                 525

Pro Gly Thr His Phe Asp Thr Thr Val Tyr Gln Thr Thr His Met Ser
    530                 535                 540

Gly Gly Ala Ile Met Gly Glu Asp Pro Lys Thr Ser Ala Val Asn Arg
545                 550                 555                 560

Tyr Leu Gln Ser Trp Asp Val Pro Asn Val Phe Val Pro Gly Ala Ser
                565                 570                 575

Ala Phe Pro Gln Gly Leu Gly Tyr Asn Pro Thr Gly Met Val Ala Ala
            580                 585                 590

Leu Thr Tyr Trp Ser Ala Lys Ala Ile Arg Glu Gln Tyr Leu Lys Asn
        595                 600                 605

Pro Gly Pro Leu Val Gln Ala
    610                 615


<210> SEQ ID NO 10
<211> LENGTH: 1323
<212> TYPE: DNA
<213> ORGANISM: Erwinia cypripedii

<400> SEQUENCE: 10

atgatgaaaa gcattctggc cctggttttg ggcacgctgt cgttcgccgc gctggcggac      60

gatcaggcaa atgacgccct ggtaaaacgg ggtgaatatc tggcgcgcgc cggtgactgc     120

gtggcctgcc acagcgtcaa aggtgggcag ccttttgccg gtgggttgcc gatggcgacg     180

ccgattggca ccatttattc caccaacatc accccggata aaaccaccgg gattggtgac     240

tatagctacg acgacttcca gaaagcggtg cgtcatggcg tggcgaaaaa cggtgacacg     300
```

```
ctgtatccgg cgatgccgta tccgtcttac gcagtggtga gcgacgagga catgaaggcg    360

ctgtacgcgt actttatgca cggcgtggcc ccggtggcgc aggctaacaa agacagcgac    420

attccgtggc cgctgtcgat gcgctggcct ttagctatct ggcgcggcgt gtttgcgccg    480

gacgtgaaag cgttccagcc tgccgcccag gaagatccgg tgctggcacg gggtcgttat    540

ctggtggaag gtctgggtca ctgtggcgcc tgccatacgc cgcgcagcat caccatgcag    600

gagaaagcgc tcagcaatga tggcgcgcat gattatctct ccggcagcag cgcaccgatt    660

gatggctgga ccgcaagcaa cctgcgtggt gacaaccgcg acggcctggg acgctggagc    720

gaggacgatc tgcgccagtt cctgcgctat ggccgcaacg atcacaccgc cgcgtttggt    780

ggtatgactg atgtggtgga gcacagcctg caacacctga gcgatgacga tatcacggca    840

attgcccgtt atctgaagtc gctgggggcg aaggacgcca gccagacggt gtttacccag    900

gatgaccagg tggcgaaagc gttgtggaaa ggtgatgaca gccagactgg cgcgtcggtg    960

tatgtcgaca gctgtgcggc ctgccataaa accgacggca gcaggttatc agcgcttctt   1020

cccggcgctg cgtggcaacc cggtggtgct ggcgaacccg atccgacgtc gctgatccac   1080

atcgtgctga ctggcggaac gctgccaggc gtgcagggtg caccgacggc gatcaccatg   1140

ccggcattcg gctggcgcct gaatgaccag caggtggcgg atgttgtgaa ctttattcgc   1200

ggcagctggg gcaacggtgc caaagccacg gtgacggcga aagatgtcgc atccttacgt   1260

aaggatgaaa ccgtgcaggc gcaccagggt aatgcggata ttaaggtgct ggagcaacag   1320

cag                                                                 1323
```

```
<210> SEQ ID NO 11
<211> LENGTH: 441
<212> TYPE: PRT
<213> ORGANISM: Erwinia cypripedii

<400> SEQUENCE: 11

Met Met Lys Ser Ile Leu Ala Leu Val Leu Gly Thr Leu Ser Phe Ala
  1               5                  10                  15

Ala Leu Ala Asp Asp Gln Ala Asn Asp Ala Leu Val Lys Arg Gly Glu
             20                  25                  30

Tyr Leu Ala Arg Ala Gly Asp Cys Val Ala Cys His Ser Val Lys Gly
         35                  40                  45

Gly Gln Pro Phe Ala Gly Gly Leu Pro Met Ala Thr Pro Ile Gly Tyr
     50                  55                  60

Ile Tyr Ser Thr Asn Ile Thr Pro Asp Lys Thr Thr Gly Ile Gly Asp
 65                  70                  75                  80

Tyr Ser Tyr Asp Asp Phe Gln Lys Ala Val Arg His Gly Val Ala Lys
                 85                  90                  95

Asn Gly Asp Thr Leu Tyr Pro Ala Met Pro Tyr Pro Ser Tyr Ala Val
            100                 105                 110

Val Ser Asp Glu Asp Met Lys Ala Leu Tyr Ala Tyr Phe Met His Gly
        115                 120                 125

Val Ala Pro Val Ala Gln Ala Asn Lys Asp Ser Asp Ile Pro Trp Pro
    130                 135                 140

Leu Ser Met Arg Trp Pro Leu Ala Ile Trp Arg Gly Val Phe Ala Pro
145                 150                 155                 160

Asp Val Lys Ala Phe Gln Pro Ala Ala Gln Glu Asp Pro Val Leu Ala
                165                 170                 175

Arg Gly Arg Tyr Leu Val Glu Gly Leu Gly His Cys Gly Ala Cys His
```

-continued

```
            180                 185                 190

Thr Pro Arg Ser Ile Thr Met Gln Glu Lys Ala Leu Ser Asn Asp Gly
        195                 200                 205

Ala His Asp Tyr Leu Ser Gly Ser Ser Ala Pro Ile Asp Gly Trp Thr
    210                 215                 220

Ala Ser Asn Leu Arg Gly Asp Asn Arg Asp Gly Leu Gly Arg Trp Ser
225                 230                 235                 240

Glu Asp Asp Leu Arg Gln Phe Leu Arg Tyr Gly Arg Asn Asp His Thr
                245                 250                 255

Ala Ala Phe Gly Gly Met Thr Asp Val Val Glu His Ser Leu Gln His
            260                 265                 270

Leu Ser Asp Asp Asp Ile Thr Ala Ile Ala Arg Tyr Leu Lys Ser Leu
        275                 280                 285

Gly Ala Lys Asp Ala Ser Gln Thr Val Phe Thr Gln Asp Asp Gln Val
    290                 295                 300

Ala Lys Ala Leu Trp Lys Gly Asp Asp Ser Gln Thr Gly Ala Ser Val
305                 310                 315                 320

Tyr Val Asp Ser Cys Ala Ala Cys His Lys Thr Asp Gly Ser Arg Leu
                325                 330                 335

Ser Ala Leu Leu Pro Gly Ala Ala Trp Gln Pro Gly Gly Ala Gly Glu
            340                 345                 350

Pro Asp Pro Thr Ser Leu Ile His Ile Val Leu Thr Gly Gly Thr Leu
        355                 360                 365

Pro Gly Val Gln Gly Ala Pro Thr Ala Ile Thr Met Pro Ala Phe Gly
    370                 375                 380

Trp Arg Leu Asn Asp Gln Gln Val Ala Asp Val Val Asn Phe Ile Arg
385                 390                 395                 400

Gly Ser Trp Gly Asn Gly Ala Lys Ala Thr Val Thr Ala Lys Asp Val
                405                 410                 415

Ala Ser Leu Arg Lys Asp Glu Thr Val Gln Ala His Gln Gly Asn Ala
            420                 425                 430

Asp Ile Lys Val Leu Glu Gln Gln Gln
        435                 440


<210> SEQ ID NO 12
<211> LENGTH: 4665
<212> TYPE: DNA
<213> ORGANISM: Erwinia cypripedii
<220> FEATURE:
<221> NAME/KEY: CDS
<222> LOCATION: (258)..(917)
<221> NAME/KEY: CDS
<222> LOCATION: (934)..(2778)
<221> NAME/KEY: CDS
<222> LOCATION: (2793)..(4115)

<400> SEQUENCE: 12

aggccttaac tgtctgtagg ctgttgtatc agaccatgac aatgtcgcgc ctgcggtgta     60

aagccgctgc gcaaaatgtt aattattttg tgcgaatttg tgtccttacg ctaaatcttt    120

gtcatcaacg gtgttacact gcgacgcaat gttaccggta acggtggcgc tgtatcctta    180

agcccgcaca taaaaatcat tacaacgcaa tcagttaacc tttcatgcca cattatatgc    240

ggcactgagg caatgtc atg tca gaa cac aaa aat ggt cac aca cgc agg       290
                   Met Ser Glu His Lys Asn Gly His Thr Arg Arg
                    1               5                  10

gat ttt ctg ctg aga acc atc acc ctg gcg cca gca atg gcg gtg ggt      338
Asp Phe Leu Leu Arg Thr Ile Thr Leu Ala Pro Ala Met Ala Val Gly
```

-continued

```
            15                  20                  25

tca aca gcg atg ggt gca ctg gtt gcg cca atg gct gcc gga gca gca      386
Ser Thr Ala Met Gly Ala Leu Val Ala Pro Met Ala Ala Gly Ala Ala
        30                  35                  40

gaa caa agc agc aaa tca caa acc gcc cgc gac tat cag ccg acc tgg      434
Glu Gln Ser Ser Lys Ser Gln Thr Ala Arg Asp Tyr Gln Pro Thr Trp
    45                  50                  55

ttt acg gcg gaa gag ttt gcc ttt atc acc gca gcg gtg gca cgt ctg      482
Phe Thr Ala Glu Glu Phe Ala Phe Ile Thr Ala Ala Val Ala Arg Leu
60                  65                  70                  75

atc ccc aac gat gaa cgt ggt cct ggc gca ctg gaa gcc ggg gtg ccg      530
Ile Pro Asn Asp Glu Arg Gly Pro Gly Ala Leu Glu Ala Gly Val Pro
                80                  85                  90

gag ttt atc gat cgc cag atg aac acc ccg tac gcc ctc ggc agc aac      578
Glu Phe Ile Asp Arg Gln Met Asn Thr Pro Tyr Ala Leu Gly Ser Asn
            95                  100                 105

tgg tac atg cag ggg ccg ttc aat ccc gat ctg ccg aaa gag ctg ggt      626
Trp Tyr Met Gln Gly Pro Phe Asn Pro Asp Leu Pro Lys Glu Leu Gly
        110                 115                 120

tat cag ctg ccg ctg gtg ccg cag cag atc tac cgt ctg ggc ctc gcc      674
Tyr Gln Leu Pro Leu Val Pro Gln Gln Ile Tyr Arg Leu Gly Leu Ala
    125                 130                 135

gat gct gat agc tgg agc aaa cac cag cac ggc aaa gtg ttt gct gag      722
Asp Ala Asp Ser Trp Ser Lys His Gln His Gly Lys Val Phe Ala Glu
140                 145                 150                 155

ctg agc ggc gac cag cag gat gcc ctg ctg agc gac ttc gaa agt ggc      770
Leu Ser Gly Asp Gln Gln Asp Ala Leu Leu Ser Asp Phe Glu Ser Gly
                160                 165                 170

aaa gcg gag ttc acc cag ctc ccg gcc aaa acc ttc ttc tcc ttc ctg      818
Lys Ala Glu Phe Thr Gln Leu Pro Ala Lys Thr Phe Phe Ser Phe Leu
            175                 180                 185

ctg caa aac acc cgc gag ggt tac ttc acg cga tcc gat cca cgg tgg      866
Leu Gln Asn Thr Arg Glu Gly Tyr Phe Thr Arg Ser Asp Pro Arg Trp
        190                 195                 200

caa tca ggg cat ggt ggg ctg gaa gct gat tgg ctt ccc cgg cgc acg      914
Gln Ser Gly His Gly Gly Leu Glu Ala Asp Trp Leu Pro Arg Arg Thr
    205                 210                 215

cgc tgattacatg gattgg gtg gaa cgc ggt gaa cgc gta tcc gtt ccc gtc    966
Arg                   Val Glu Arg Gly Glu Arg Val Ser Val Pro Val
220                                   225                 230

agt gga tat tcg cgg gga gag ggc gta acc gtg gca aat gaa ttg aag     1014
Ser Gly Tyr Ser Arg Gly Glu Gly Val Thr Val Ala Asn Glu Leu Lys
            235                 240                 245

aaa gtg gat gcg gtg gtg gtg ggt ttc ggc tgg gcc ggt gcc atc atg     1062
Lys Val Asp Ala Val Val Val Gly Phe Gly Trp Ala Gly Ala Ile Met
        250                 255                 260

gca aaa gaa ctg acc gaa gcc ggg ctg aat gtg gtg gcg ctg gag cgt     1110
Ala Lys Glu Leu Thr Glu Ala Gly Leu Asn Val Val Ala Leu Glu Arg
    265                 270                 275

ggt ccg cat cgt gac acc tac ccg gat ggc gcg tat ccg caa tcc att     1158
Gly Pro His Arg Asp Thr Tyr Pro Asp Gly Ala Tyr Pro Gln Ser Ile
280                 285                 290                 295

gat gaa ctg acc tac aac atc cgt aaa aag ctg ttc cag gac ctg tca     1206
Asp Glu Leu Thr Tyr Asn Ile Arg Lys Lys Leu Phe Gln Asp Leu Ser
                300                 305                 310

aaa agc acc gtc acc att cgt cac gac gcg tca cag acg gca gtg ccg     1254
Lys Ser Thr Val Thr Ile Arg His Asp Ala Ser Gln Thr Ala Val Pro
            315                 320                 325

tat cgt cag ctg gcg gcg ttt ctg ccc ggc acc ggt acc ggc ggc gcg     1302
```

-continued

```
Tyr Arg Gln Leu Ala Ala Phe Leu Pro Gly Thr Gly Thr Gly Gly Ala
        330                 335                 340

ggc ctg cac tgg tca ggc gta cat ttc cgt gtc gac ccg gtc gag ctg     1350
Gly Leu His Trp Ser Gly Val His Phe Arg Val Asp Pro Val Glu Leu
    345                 350                 355

aat ctg cgc agc cat tat gaa gcg cgt tac ggc aaa aac ttt atc ccg     1398
Asn Leu Arg Ser His Tyr Glu Ala Arg Tyr Gly Lys Asn Phe Ile Pro
360                 365                 370                 375

gaa ggc atg acg att cag gat ttc ggc gtc agc tat aac gaa ctg gaa     1446
Glu Gly Met Thr Ile Gln Asp Phe Gly Val Ser Tyr Asn Glu Leu Glu
                380                 385                 390

ccc ttc ttc gat cag gcg gag aaa gtc ttt ggt acc tcg ggc agt gcc     1494
Pro Phe Phe Asp Gln Ala Glu Lys Val Phe Gly Thr Ser Gly Ser Ala
            395                 400                 405

tgg acc atc aaa ggc aag atg atc ggc aag gag aaa ggc ggc aac ttt     1542
Trp Thr Ile Lys Gly Lys Met Ile Gly Lys Glu Lys Gly Gly Asn Phe
        410                 415                 420

tac gcg ccg gac cgc tcc agc gac ttc ccg ctg ccc gca cag aag cgg     1590
Tyr Ala Pro Asp Arg Ser Ser Asp Phe Pro Leu Pro Ala Gln Lys Arg
    425                 430                 435

act tac tcg gcg cag ctg ttt gcc cag gcg gca gag tcg gtg ggc tat     1638
Thr Tyr Ser Ala Gln Leu Phe Ala Gln Ala Ala Glu Ser Val Gly Tyr
440                 445                 450                 455

cat ccg tac gat atg cca tcg gcc aac acc tca ggt ccg tac acc aac     1686
His Pro Tyr Asp Met Pro Ser Ala Asn Thr Ser Gly Pro Tyr Thr Asn
                460                 465                 470

acc tac ggc gca cag atg ggc ccg tgc aac ttc tgc ggc tat tgc agc     1734
Thr Tyr Gly Ala Gln Met Gly Pro Cys Asn Phe Cys Gly Tyr Cys Ser
            475                 480                 485

ggc tac gcc tgc tac atg tat tcc aaa gcg tcg cct aac gtg aac atc     1782
Gly Tyr Ala Cys Tyr Met Tyr Ser Lys Ala Ser Pro Asn Val Asn Ile
        490                 495                 500

ctg ccc gcg ctg cgt cag gag ccg aag ttt gag ctg cgt aac aac gca     1830
Leu Pro Ala Leu Arg Gln Glu Pro Lys Phe Glu Leu Arg Asn Asn Ala
    505                 510                 515

tat gtg ttg cgc gtc aat ctg acc ggc gac aaa aaa cgc gcc act ggc     1878
Tyr Val Leu Arg Val Asn Leu Thr Gly Asp Lys Lys Arg Ala Thr Gly
520                 525                 530                 535

gtg acc tat ctc gat ggt cag ggt cgt gaa gtg gtg cag cct gcg gat     1926
Val Thr Tyr Leu Asp Gly Gln Gly Arg Glu Val Val Gln Pro Ala Asp
                540                 545                 550

ctg gtg atc ctg tca gcg ttc cag ttc cac aac gtg cac ctg atg ctg     1974
Leu Val Ile Leu Ser Ala Phe Gln Phe His Asn Val His Leu Met Leu
            555                 560                 565

ctg tcc ggt atc ggc cag ccg tat aac ccg atc act aac gaa ggt gtg     2022
Leu Ser Gly Ile Gly Gln Pro Tyr Asn Pro Ile Thr Asn Glu Gly Val
        570                 575                 580

gtc ggc cgt aac ttc gct tat cag aac atc tcg acg ctg aaa gcg ctg     2070
Val Gly Arg Asn Phe Ala Tyr Gln Asn Ile Ser Thr Leu Lys Ala Leu
    585                 590                 595

ttc gac aaa aac acc acc act aac ccg ttt atc ggt gcg ggt ggc gca     2118
Phe Asp Lys Asn Thr Thr Thr Asn Pro Phe Ile Gly Ala Gly Gly Ala
600                 605                 610                 615

ggg gtg gcg gtg gat gat ttc aac gcc gac aac ttc gac cac ggc ccg     2166
Gly Val Ala Val Asp Asp Phe Asn Ala Asp Asn Phe Asp His Gly Pro
                620                 625                 630

tac ggc ttc gtc ggt ggc tcg cca ttc tgg gtg aac cag gcg ggt acc     2214
Tyr Gly Phe Val Gly Gly Ser Pro Phe Trp Val Asn Gln Ala Gly Thr
            635                 640                 645
```

-continued

```
aaa ccg gtt tcc ggt ctg ccg acc ccc aaa ggc acg ccg aac tgg ggc      2262
Lys Pro Val Ser Gly Leu Pro Thr Pro Lys Gly Thr Pro Asn Trp Gly
        650                 655                 660

agc cag tgg aaa gcg gcg gtg gcg gat acc tac aac cac cat att tcg      2310
Ser Gln Trp Lys Ala Ala Val Ala Asp Thr Tyr Asn His His Ile Ser
    665                 670                 675

atg gat gcc cac ggt gcg cac cag tca tac cgc gct aac tac ctc gat      2358
Met Asp Ala His Gly Ala His Gln Ser Tyr Arg Ala Asn Tyr Leu Asp
680                 685                 690                 695

ctc gat ccg aac tac aaa aat gtc tac ggc cag ccg ctg ctg cgt atg      2406
Leu Asp Pro Asn Tyr Lys Asn Val Tyr Gly Gln Pro Leu Leu Arg Met
                700                 705                 710

acc ttt gac tgg cag gac aac gac atc agg atg gcg cag ttt atg gtc      2454
Thr Phe Asp Trp Gln Asp Asn Asp Ile Arg Met Ala Gln Phe Met Val
            715                 720                 725

ggc aag atg cgc aaa atc acc gag gcc atg aat ccg aag atg atc atc      2502
Gly Lys Met Arg Lys Ile Thr Glu Ala Met Asn Pro Lys Met Ile Ile
        730                 735                 740

ggc ggc gct aag gga ccg ggt acc cac ttc gat acc acc gtg tat caa      2550
Gly Gly Ala Lys Gly Pro Gly Thr His Phe Asp Thr Thr Val Tyr Gln
    745                 750                 755

acc acg cat atg agc ggc ggg gcg atc atg ggt gaa gat ccg aaa acc      2598
Thr Thr His Met Ser Gly Gly Ala Ile Met Gly Glu Asp Pro Lys Thr
760                 765                 770                 775

agc gca gtg aac cgt tat ttg cag agc tgg gat gtg ccg aac gtg ttt      2646
Ser Ala Val Asn Arg Tyr Leu Gln Ser Trp Asp Val Pro Asn Val Phe
                780                 785                 790

gtg ccg ggt gcg tcc gcg ttc ccg cag ggt ctg ggc tac aac ccg acc      2694
Val Pro Gly Ala Ser Ala Phe Pro Gln Gly Leu Gly Tyr Asn Pro Thr
            795                 800                 805

ggc atg gtg gcg gca ctg acc tac tgg tcg gcg aaa gcc atc cgt gaa      2742
Gly Met Val Ala Ala Leu Thr Tyr Trp Ser Ala Lys Ala Ile Arg Glu
        810                 815                 820

cag tat ctg aag aac cca ggt cca ctg gtg cag gca taaggaaaac ggcg      2792
Gln Tyr Leu Lys Asn Pro Gly Pro Leu Val Gln Ala
    825                 830                 835

atg atg aaa agc att ctg gcc ctg gtt ttg ggc acg ctg tcg ttc gcc      2840
Met Met Lys Ser Ile Leu Ala Leu Val Leu Gly Thr Leu Ser Phe Ala
                840                 845                 850

gcg ctg gcg gac gat cag gca aat gac gcc ctg gta aaa cgg ggt gaa      2888
Ala Leu Ala Asp Asp Gln Ala Asn Asp Ala Leu Val Lys Arg Gly Glu
            855                 860                 865

tat ctg gcg cgc gcc ggt gac tgc gtg gcc tgc cac agc gtc aaa ggt      2936
Tyr Leu Ala Arg Ala Gly Asp Cys Val Ala Cys His Ser Val Lys Gly
        870                 875                 880

ggg cag cct ttt gcc ggt ggg ttg ccg atg gcg acg ccg att ggc acc      2984
Gly Gln Pro Phe Ala Gly Gly Leu Pro Met Ala Thr Pro Ile Gly Thr
    885                 890                 895

att tat tcc acc aac atc acc ccg gat aaa acc acc ggg att ggt gac      3032
Ile Tyr Ser Thr Asn Ile Thr Pro Asp Lys Thr Thr Gly Ile Gly Asp
900                 905                 910                 915

tat agc tac gac gac ttc cag aaa gcg gtg cgt cat ggc gtg gcg aaa      3080
Tyr Ser Tyr Asp Asp Phe Gln Lys Ala Val Arg His Gly Val Ala Lys
                920                 925                 930

aac ggt gac acg ctg tat ccg gcg atg ccg tat ccg tct tac gca gtg      3128
Asn Gly Asp Thr Leu Tyr Pro Ala Met Pro Tyr Pro Ser Tyr Ala Val
            935                 940                 945

gtg agc gac gag gac atg aag gcg ctg tac gcg tac ttt atg cac ggc      3176
Val Ser Asp Glu Asp Met Lys Ala Leu Tyr Ala Tyr Phe Met His Gly
        950                 955                 960
```

-continued

```
gtg gcc ccg gtg gcg cag gct aac aaa gac agc gac att ccg tgg ccg     3224
Val Ala Pro Val Ala Gln Ala Asn Lys Asp Ser Asp Ile Pro Trp Pro
    965                 970                 975

ctg tcg atg cgc tgg cct tta gct atc tgg cgc ggc gtg ttt gcg ccg     3272
Leu Ser Met Arg Trp Pro Leu Ala Ile Trp Arg Gly Val Phe Ala Pro
980                 985                 990                 995

gac gtg aaa gcg ttc cag cct gcc gcc cag gaa gat ccg gtg ctg gca     3320
Asp Val Lys Ala Phe Gln Pro Ala Ala Gln Glu Asp Pro Val Leu Ala
                1000                1005                1010

cgg ggt cgt tat ctg gtg gaa ggt ctg ggt cac tgt ggc gcc tgc cat     3368
Arg Gly Arg Tyr Leu Val Glu Gly Leu Gly His Cys Gly Ala Cys His
            1015                1020                1025

acg ccg cgc agc atc acc atg cag gag aaa gcg ctc agc aat gat ggc     3416
Thr Pro Arg Ser Ile Thr Met Gln Glu Lys Ala Leu Ser Asn Asp Gly
        1030                1035                1040

gcg cat gat tat ctc tcc ggc agc agc gca ccg att gat ggc tgg acc     3464
Ala His Asp Tyr Leu Ser Gly Ser Ser Ala Pro Ile Asp Gly Trp Thr
    1045                1050                1055

gca agc aac ctg cgt ggt gac aac cgc gac ggc ctg gga cgc tgg agc     3512
Ala Ser Asn Leu Arg Gly Asp Asn Arg Asp Gly Leu Gly Arg Trp Ser
1060                1065                1070                1075

gag gac gat ctg cgc cag ttc ctg cgc tat ggc cgc aac gat cac acc     3560
Glu Asp Asp Leu Arg Gln Phe Leu Arg Tyr Gly Arg Asn Asp His Thr
                1080                1085                1090

gcc gcg ttt ggt ggt atg act gat gtg gtg gag cac agc ctg caa cac     3608
Ala Ala Phe Gly Gly Met Thr Asp Val Val Glu His Ser Leu Gln His
            1095                1100                1105

ctg agc gat gac gat atc acg gca att gcc cgt tat ctg aag tcg ctg     3656
Leu Ser Asp Asp Asp Ile Thr Ala Ile Ala Arg Tyr Leu Lys Ser Leu
        1110                1115                1120

ggg gcg aag gac gcc agc cag acg gtg ttt acc cag gat gac cag gtg     3704
Gly Ala Lys Asp Ala Ser Gln Thr Val Phe Thr Gln Asp Asp Gln Val
    1125                1130                1135

gcg aaa gcg ttg tgg aaa ggt gat gac agc cag act ggc gcg tcg gtg     3752
Ala Lys Ala Leu Trp Lys Gly Asp Asp Ser Gln Thr Gly Ala Ser Val
1140                1145                1150                1155

tat gtc gac agc tgt gcg gcc tgc cat aaa acc gac ggc agc agg tta     3800
Tyr Val Asp Ser Cys Ala Ala Cys His Lys Thr Asp Gly Ser Arg Leu
                1160                1165                1170

tca gcg ctt ctt ccc ggc gct gcg tgg caa ccc ggt ggt gct ggc gaa     3848
Ser Ala Leu Leu Pro Gly Ala Ala Trp Gln Pro Gly Gly Ala Gly Glu
            1175                1180                1185

ccc gat ccg acg tcg ctg atc cac atc gtg ctg act ggc gga acg ctg     3896
Pro Asp Pro Thr Ser Leu Ile His Ile Val Leu Thr Gly Gly Thr Leu
        1190                1195                1200

cca ggc gtg cag ggt gca ccg acg gcg atc acc atg ccg gca ttc ggc     3944
Pro Gly Val Gln Gly Ala Pro Thr Ala Ile Thr Met Pro Ala Phe Gly
    1205                1210                1215

tgg cgc ctg aat gac cag cag gtg gcg gat gtt gtg aac ttt att cgc     3992
Trp Arg Leu Asn Asp Gln Gln Val Ala Asp Val Val Asn Phe Ile Arg
1220                1225                1230                1235

ggc agc tgg ggc aac ggt gcc aaa gcc acg gtg acg gcg aaa gat gtc     4040
Gly Ser Trp Gly Asn Gly Ala Lys Ala Thr Val Thr Ala Lys Asp Val
                1240                1245                1250

gca tcc tta cgt aag gat gaa acc gtg cag gcg cac cag ggt aat gcg     4088
Ala Ser Leu Arg Lys Asp Glu Thr Val Gln Ala His Gln Gly Asn Ala
            1255                1260                1265

gat att aag gtg ctg gag caa cag cag taatattacg tttgccacga           4135
Asp Ile Lys Val Leu Glu Gln Gln Gln
```

-continued

```
      1270                1275

ggggatttcg ttcgcctcgg agtgatttcg ttcgctatgg gcactggcag tttcagctcg   4195

ccagtgcggc gaccgagcaa aggggacctg gccgtcccct ttgcattccc cggccttgcg   4255

ccgccttcct cgccgcttcg cggctttttc gcgcgataaa tcgcgccgct acacgccgcc   4315

tttcgccgca tccttgcggc tcatcctgga atcgctcccg cgctcagcga gtccggatgg   4375

cgctcacacc cccgctgcaa ccgcgatgac ggtctttggt tttcttttg ttgtttgttt    4435

ttatgagatg gtcttgcaga cggcggtgtt ggcggcattc gcagcgccga gtgcagaagg   4495

aaggccagga cgagtcgcat ggatgcgacg agagcgcggc atggcgcgga ttgcaaaggt   4555

ccgcgccctc ggacctttgc ccgtccgcct gcacaggcgg ccctgaaact gcctaaagcc   4615

tggcgggcgg aacccctgcg gagctaaacc ggtgccagcg attaaatatt              4665


<210> SEQ ID NO 13
<211> LENGTH: 1276
<212> TYPE: PRT
<213> ORGANISM: Erwinia cypripedii

<400> SEQUENCE: 13

Met Ser Glu His Lys Asn Gly His Thr Arg Arg Asp Phe Leu Leu Arg
  1               5                  10                  15

Thr Ile Thr Leu Ala Pro Ala Met Ala Val Gly Ser Thr Ala Met Gly
             20                  25                  30

Ala Leu Val Ala Pro Met Ala Ala Gly Ala Ala Glu Gln Ser Ser Lys
         35                  40                  45

Ser Gln Thr Ala Arg Asp Tyr Gln Pro Thr Trp Phe Thr Ala Glu Glu
     50                  55                  60

Phe Ala Phe Ile Thr Ala Ala Val Ala Arg Leu Ile Pro Asn Asp Glu
 65                  70                  75                  80

Arg Gly Pro Gly Ala Leu Glu Ala Gly Val Pro Glu Phe Ile Asp Arg
                 85                  90                  95

Gln Met Asn Thr Pro Tyr Ala Leu Gly Ser Asn Trp Tyr Met Gln Gly
            100                 105                 110

Pro Phe Asn Pro Asp Leu Pro Lys Glu Leu Gly Tyr Gln Leu Pro Leu
        115                 120                 125

Val Pro Gln Gln Ile Tyr Arg Leu Gly Leu Ala Asp Ala Asp Ser Trp
    130                 135                 140

Ser Lys His Gln His Gly Lys Val Phe Ala Glu Leu Ser Gly Asp Gln
145                 150                 155                 160

Gln Asp Ala Leu Leu Ser Asp Phe Glu Ser Gly Lys Ala Glu Phe Thr
                165                 170                 175

Gln Leu Pro Ala Lys Thr Phe Phe Ser Phe Leu Leu Gln Asn Thr Arg
            180                 185                 190

Glu Gly Tyr Phe Thr Arg Ser Asp Pro Arg Trp Gln Ser Gly His Gly
        195                 200                 205

Gly Leu Glu Ala Asp Trp Leu Pro Arg Arg Thr Arg Val Glu Arg Gly
    210                 215                 220

Glu Arg Val Ser Val Pro Val Ser Gly Tyr Ser Arg Gly Glu Gly Val
225                 230                 235                 240

Thr Val Ala Asn Glu Leu Lys Lys Val Asp Ala Val Val Val Gly Phe
                245                 250                 255

Gly Trp Ala Gly Ala Ile Met Ala Lys Glu Leu Thr Glu Ala Gly Leu
            260                 265                 270
```

-continued

```
Asn Val Val Ala Leu Glu Arg Gly Pro His Arg Asp Thr Tyr Pro Asp
        275                 280                 285

Gly Ala Tyr Pro Gln Ser Ile Asp Glu Leu Thr Tyr Asn Ile Arg Lys
    290                 295                 300

Lys Leu Phe Gln Asp Leu Ser Lys Ser Thr Val Thr Ile Arg His Asp
305                 310                 315                 320

Ala Ser Gln Thr Ala Val Pro Tyr Arg Gln Leu Ala Ala Phe Leu Pro
                325                 330                 335

Gly Thr Gly Thr Gly Gly Ala Gly Leu His Trp Ser Gly Val His Phe
            340                 345                 350

Arg Val Asp Pro Val Glu Leu Asn Leu Arg Ser His Tyr Glu Ala Arg
        355                 360                 365

Tyr Gly Lys Asn Phe Ile Pro Glu Gly Met Thr Ile Gln Asp Phe Gly
    370                 375                 380

Val Ser Tyr Asn Glu Leu Glu Pro Phe Phe Asp Gln Ala Glu Lys Val
385                 390                 395                 400

Phe Gly Thr Ser Gly Ser Ala Trp Thr Ile Lys Gly Lys Met Ile Gly
                405                 410                 415

Lys Glu Lys Gly Gly Asn Phe Tyr Ala Pro Asp Arg Ser Ser Asp Phe
            420                 425                 430

Pro Leu Pro Ala Gln Lys Arg Thr Tyr Ser Ala Gln Leu Phe Ala Gln
        435                 440                 445

Ala Ala Glu Ser Val Gly Tyr His Pro Tyr Asp Met Pro Ser Ala Asn
    450                 455                 460

Thr Ser Gly Pro Tyr Thr Asn Thr Tyr Gly Ala Gln Met Gly Pro Cys
465                 470                 475                 480

Asn Phe Cys Gly Tyr Cys Ser Gly Tyr Ala Cys Tyr Met Tyr Ser Lys
                485                 490                 495

Ala Ser Pro Asn Val Asn Ile Leu Pro Ala Leu Arg Gln Glu Pro Lys
            500                 505                 510

Phe Glu Leu Arg Asn Asn Ala Tyr Val Leu Arg Val Asn Leu Thr Gly
        515                 520                 525

Asp Lys Lys Arg Ala Thr Gly Val Thr Tyr Leu Asp Gly Gln Gly Arg
    530                 535                 540

Glu Val Val Gln Pro Ala Asp Leu Val Ile Leu Ser Ala Phe Gln Phe
545                 550                 555                 560

His Asn Val His Leu Met Leu Leu Ser Gly Ile Gly Gln Pro Tyr Asn
                565                 570                 575

Pro Ile Thr Asn Glu Gly Val Val Gly Arg Asn Phe Ala Tyr Gln Asn
            580                 585                 590

Ile Ser Thr Leu Lys Ala Leu Phe Asp Lys Asn Thr Thr Thr Asn Pro
        595                 600                 605

Phe Ile Gly Ala Gly Gly Ala Gly Val Ala Val Asp Asp Phe Asn Ala
    610                 615                 620

Asp Asn Phe Asp His Gly Pro Tyr Gly Phe Val Gly Gly Ser Pro Phe
625                 630                 635                 640

Trp Val Asn Gln Ala Gly Thr Lys Pro Val Ser Gly Leu Pro Thr Pro
                645                 650                 655

Lys Gly Thr Pro Asn Trp Gly Ser Gln Trp Lys Ala Ala Val Ala Asp
            660                 665                 670

Thr Tyr Asn His His Ile Ser Met Asp Ala His Gly Ala His Gln Ser
        675                 680                 685

Tyr Arg Ala Asn Tyr Leu Asp Leu Asp Pro Asn Tyr Lys Asn Val Tyr
```

-continued

```
    690                 695                 700

Gly Gln Pro Leu Leu Arg Met Thr Phe Asp Trp Gln Asp Asn Asp Ile
705                 710                 715                 720

Arg Met Ala Gln Phe Met Val Gly Lys Met Arg Lys Ile Thr Glu Ala
                725                 730                 735

Met Asn Pro Lys Met Ile Ile Gly Gly Ala Lys Gly Pro Gly Thr His
            740                 745                 750

Phe Asp Thr Thr Val Tyr Gln Thr Thr His Met Ser Gly Gly Ala Ile
        755                 760                 765

Met Gly Glu Asp Pro Lys Thr Ser Ala Val Asn Arg Tyr Leu Gln Ser
    770                 775                 780

Trp Asp Val Pro Asn Val Phe Val Pro Gly Ala Ser Ala Phe Pro Gln
785                 790                 795                 800

Gly Leu Gly Tyr Asn Pro Thr Gly Met Val Ala Ala Leu Thr Tyr Trp
                805                 810                 815

Ser Ala Lys Ala Ile Arg Glu Gln Tyr Leu Lys Asn Pro Gly Pro Leu
            820                 825                 830

Val Gln Ala Met Met Lys Ser Ile Leu Ala Leu Val Leu Gly Thr Leu
        835                 840                 845

Ser Phe Ala Ala Leu Ala Asp Asp Gln Ala Asn Asp Ala Leu Val Lys
    850                 855                 860

Arg Gly Glu Tyr Leu Ala Arg Ala Gly Asp Cys Val Ala Cys His Ser
865                 870                 875                 880

Val Lys Gly Gly Gln Pro Phe Ala Gly Gly Leu Pro Met Ala Thr Pro
                885                 890                 895

Ile Gly Thr Ile Tyr Ser Thr Asn Ile Thr Pro Asp Lys Thr Thr Gly
            900                 905                 910

Ile Gly Asp Tyr Ser Tyr Asp Asp Phe Gln Lys Ala Val Arg His Gly
        915                 920                 925

Val Ala Lys Asn Gly Asp Thr Leu Tyr Pro Ala Met Pro Tyr Pro Ser
    930                 935                 940

Tyr Ala Val Val Ser Asp Glu Asp Met Lys Ala Leu Tyr Ala Tyr Phe
945                 950                 955                 960

Met His Gly Val Ala Pro Val Ala Gln Ala Asn Lys Asp Ser Asp Ile
                965                 970                 975

Pro Trp Pro Leu Ser Met Arg Trp Pro Leu Ala Ile Trp Arg Gly Val
            980                 985                 990

Phe Ala Pro Asp Val Lys Ala Phe Gln Pro Ala Ala Gln Glu Asp Pro
        995                1000                1005

Val Leu Ala Arg Gly Arg Tyr Leu Val Glu Gly Leu Gly His Cys Gly
   1010                1015                1020

Ala Cys His Thr Pro Arg Ser Ile Thr Met Gln Glu Lys Ala Leu Ser
1025               1030                1035                1040

Asn Asp Gly Ala His Asp Tyr Leu Ser Gly Ser Ser Ala Pro Ile Asp
               1045                1050                1055

Gly Trp Thr Ala Ser Asn Leu Arg Gly Asp Asn Arg Asp Gly Leu Gly
           1060                1065                1070

Arg Trp Ser Glu Asp Asp Leu Arg Gln Phe Leu Arg Tyr Gly Arg Asn
       1075                1080                1085

Asp His Thr Ala Ala Phe Gly Gly Met Thr Asp Val Val Glu His Ser
   1090                1095                1100

Leu Gln His Leu Ser Asp Asp Asp Ile Thr Ala Ile Ala Arg Tyr Leu
1105               1110                1115                1120
```

-continued

```
Lys Ser Leu Gly Ala Lys Asp Ala Ser Gln Thr Val Phe Thr Gln Asp
               1125                1130                1135

Asp Gln Val Ala Lys Ala Leu Trp Lys Gly Asp Asp Ser Gln Thr Gly
           1140                1145                1150

Ala Ser Val Tyr Val Asp Ser Cys Ala Ala Cys His Lys Thr Asp Gly
       1155                1160                1165

Ser Arg Leu Ser Ala Leu Leu Pro Gly Ala Ala Trp Gln Pro Gly Gly
   1170                1175                1180

Ala Gly Glu Pro Asp Pro Thr Ser Leu Ile His Ile Val Leu Thr Gly
1185                1190                1195                1200

Gly Thr Leu Pro Gly Val Gln Gly Ala Pro Thr Ala Ile Thr Met Pro
               1205                1210                1215

Ala Phe Gly Trp Arg Leu Asn Asp Gln Gln Val Ala Asp Val Val Asn
           1220                1225                1230

Phe Ile Arg Gly Ser Trp Gly Asn Gly Ala Lys Ala Thr Val Thr Ala
       1235                1240                1245

Lys Asp Val Ala Ser Leu Arg Lys Asp Glu Thr Val Gln Ala His Gln
   1250                1255                1260

Gly Asn Ala Asp Ile Lys Val Leu Glu Gln Gln Gln
1265                1270                1275
```